United States Patent
Herald, Jr. et al.

[11] Patent Number: 5,493,348
[45] Date of Patent: Feb. 20, 1996

[54] MEANS FOR MOUNTING A PRESCRIPTION LENS ACCESSORY ONTO A PAIR OF GLASSES

[75] Inventors: A. Glen Herald, Jr., Collierville, Tenn.; John Chin, Tainan, Taiwan

[73] Assignee: Crews, Inc., Memphis, Tenn.

[21] Appl. No.: 392,443

[22] Filed: Feb. 22, 1995

[51] Int. Cl.⁶ .................................................. G02C 7/08
[52] U.S. Cl. ........................... 351/57; 351/149; 351/158; 2/444
[58] Field of Search ................................ 351/41, 44, 47, 351/57, 118, 149, 158, 155; 2/444, 13

[56] References Cited

U.S. PATENT DOCUMENTS

| | | | |
|---|---|---|---|
| 2,714,717 | 8/1955 | Allman | 2/13 |
| 2,752,598 | 7/1956 | Abels | 2/13 |
| 2,923,943 | 2/1960 | Rubin | 2/13 |
| 3,787,113 | 1/1974 | Shedrow | 351/43 |
| 4,257,691 | 3/1981 | Brooks | 351/158 |
| 4,349,251 | 9/1982 | Shedrow | 351/128 |
| 4,620,778 | 11/1986 | Bertolli | 351/51 |
| 4,955,708 | 9/1990 | Kahaney | 351/44 |
| 5,018,223 | 5/1991 | Dawson et al. | 2/436 |
| 5,187,503 | 11/1995 | Hilton | 351/128 |
| 5,335,025 | 8/1994 | Wang | 351/47 |
| 5,376,977 | 12/1994 | Liu | 351/47 |

Primary Examiner—William L. Sikes
Assistant Examiner—Huy Mai
Attorney, Agent, or Firm—Edwin E. Greigg; Ronald E. Greigg

[57] ABSTRACT

A pair of glasses to which an eyeglass accessory is secured by use of at least one T-slot on the pair of glasses and a complementally-shaped T-bar on the eyeglass accessory. In a preferred embodiment the eyeglass accessory allows corrective prescription lenses to be mounted inside a pair of safety glasses.

10 Claims, 1 Drawing Sheet

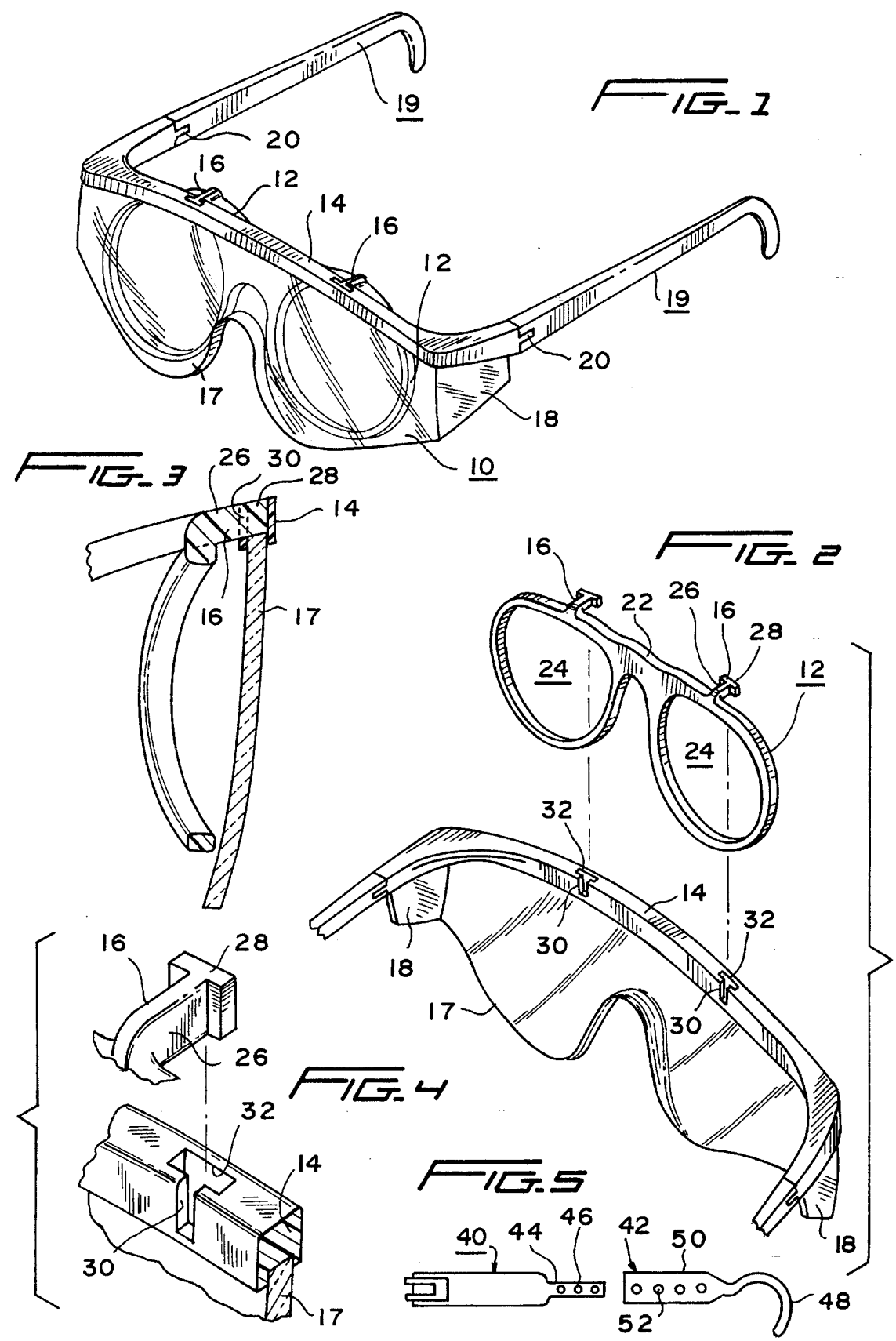

MEANS FOR MOUNTING A PRESCRIPTION LENS ACCESSORY ONTO A PAIR OF GLASSES

BACKGROUND OF THE INVENTION

This invention is directed to improvements in spectacles, glasses, face mask, goggles, and the like and more particularly, to a pair of safety glasses to which accessory prescription lenses can be secured.

Heretofore, different types of glasses, frames, mask, goggles, etc., have been made. Some prior devices have been patented for attaching sunglasses to a pair of glasses, prescription glasses to safety glasses, etc. Such patents include the following: U.S. Pat. Nos. 2,714,717; 2,752,598; 2,923,943; 3,787,113; 4,257,691; 4,349,251; 4,620,778; 4,955,708; 5,018,223 and 5,335,025. These glasses have various uses and some are equipped to support accessory glasses, such as sunglasses, prescription lenses, etc.

OBJECTS AND SUMMARY OF THE INVENTION

It is therefore a principal object of this invention to provide for a quick easy assembly and disassembly of prescription or other types of glasses onto another pair of glasses, such as safety glasses.

Another object is to provide a pair of glasses of different types to which an eye glass accessory can be secured for different purposes such as sunglass protection, prescription lenses, safety glasses, etc.

Still another object is to provide means for securing an eyeglass accessory onto a pair of glasses such that the accessory does not affect the wearability of the basic glasses to which the accessory is secured.

Yet another object is to provide a separate set of lenses which can be added to a pair of eyeglasses without changing the relationship of the pair of eyeglasses with respect to the face, nose, etc.

The invention will be better understood and further objects and advantages thereof will become more apparent from the ensuing detailed description of a preferred embodiment taken in conjunction with the drawings.

BRIEF DESCRIPTION OF THE DRAWINGS

FIG. 1 illustrates a pair of safety glasses including a frame or brow bar to which an accessory prescription lenses have been secured for use with the safety glasses;

FIG. 2 illustrates an exploded view of a pair of safety glasses with a prescription lens accessory spaced therefrom for assembly onto the frame of the safety glasses;

FIG. 3 illustrates a section along the T-tab of the prescription lens accessory showing the same in place on the frame of the safety glasses;

FIG. 4 is an enlarged view illustrating a connection tab of a prescription lens accessory spaced from a complementally-formed reception opening or T-slot by which the accessory is secured to the safety glasses; and FIG. 5 illustrates adjustable temples for adjusting the length of the glasses for differently sized heads.

DETAILED DESCRIPTION OF THE INVENTION

Now referring to the drawings there is shown in FIG. 1 a pair of safety glasses 10 to which a prescription lens accessory 12 has been secured to the frame 14 of the safety glasses by a pair of T-shaped tabs 16 such that the prescription lenses are positioned on the inside surface of the safety glasses. As shown, the safety glasses have one lens 17, however, it could have two separate lenses. The single lens shown is made of one piece of plastic or safety glass with the one piece lens secured to a frame portion 14 which is secured over the upper edge surface of the one piece lens. The lens is shown with opposite side portions 18 that extend along the face to which the temples 19 are secured by a hinge 20. In the embodiment shown the frame 14 constitutes a brow bar only to which a single plastic lens is attached.

As best shown in FIG. 2, the prescription lens accessory is shown with a frame 22 in which a pair of prescription lenses are secured. The frame 22 is provided with a pair of spaced T-shaped tabs 16 which are wider in a vertical direction than in a horizontal direction. Each T-bar 16 has a projecting leg 26 of the T-bar connected with the frame 22 and a cross piece 28 of the T-bar which is shaped to fit tightly into a complementally-shaped T-slot in the brow bar or frame 14. The T-slot has an opening 30 to the back side of the frame 14 and a closed cross slot 32 within the frame 14. As shown in FIGS. 1 and 3 the T-bar 16 fits into the T-slot so that the prescription lenses accessory is secured firmly to the brow bar or frame of the safety glasses.

FIGS. 1 and 2 illustrate the T-bar and T-slot such that the prescription lens accessory is disposed on the inside of the safety glasses. One can view FIG. 4 as if the T-bar and T-slot are such that the prescription glasses could be secured on the outside of the safety glasses. This would require making the T-bars 16 such that they would protrude from the opposite side shown in FIG. 2 so that the correct lens of the prescription lens accessory would be in front of the correct eye. Thus, the prescription lens accessory could be on the outside of the safety glass lens by properly forming the T-tabs and T-slots so that the prescription glasses can be mounted on the outside of the safety glasses. Similarly, instead of prescription lenses, the lens accessory could be provided with sunglass lenses and fitted outwardly upon normal eyeglasses.

It would be obvious to one skilled in the art that the safety glass lens could be made of glass or plastic of uniform thickness, etc. Without any corrective measures so that the safety glasses could be worn by any person whether they required corrective glasses or not. The purpose for the prescription lenses to be separate and mountable onto the safety glasses is that a common safety glass lens frame can be made available for every user and only those persons requiring the use of corrective lenses need have the prescription lenses accessory made special for such persons.

In order to adjust the safety glasses for different shaped faces, and head sizes, which may require a different distance between the safety glass brow bar and the ears, the temples 19 can be made adjustable as shown in FIG. 5. Adjustable length temples can be made by forming each temple into two pieces 40, 42. One piece 40 will be hinged and extend backwardly from the frame or lens. This piece will have a leg portion 44 with a plurality of spaced protrusions 46 along a portion of its length. The ear engaging portion 48 will have a sleeve portion 50 with a plurality of same spaced apertures 52 into which some of the protrusions will fit. Thus, the sleeve portion 50 can be adjusted relative to the leg portion for different lengths of the temples.

The proposed combination of safety glasses and prescription lens accessory mounted as set forth herein above avoids any projections which may be harmful to the face, nose, eyes, etc. The T-tab and T-slot are compatible so that the T-tab fits into the T-slot without any portion projecting from the safety glass frame except the leg that connects the T-tab to the frame of the prescription lens accessory. Each of the frames may be made of plastic and the T-tab and T-slot are made to have a tight fit so that the prescription lens accessory will not readily detach from the safety glass frame.

The disclosure has been set forth such that safety glasses and prescription glasses are being used in combination. It would be obvious to one skilled in the art that the basic glasses can be of any type, such as sunglasses, with a mounting means such as described above.

The foregoing relates to a preferred exemplary embodiment of the invention, it being understood that other variants and embodiments thereof are possible within the spirit and scope of the invention, the latter being defined by the appended claims.

What is claimed:

1. Mounting means for mounting an eyeglass accessory onto a pair of glasses in which:

said pair of glasses include a frame portion, said frame portion of said pair of glasses includes at least one T-slot, and said eyeglass accessory having lens means including at least one projecting T-bar which interfits into said at least one T-slot in said frame portion of said pair of glasses in order to mount said eyeglass accessory onto said pair of glasses.

2. A mounting means as set forth in claim 1, wherein said eyeglass accessory includes prescription lenses, and said pair of glasses are safety glasses.

3. Mounting means as set forth in claim 2 in which:

said at least one T-slot has one portion which forms a vertical opening in the frame of said safety glasses frame, and one closed portion which extends transversely of said vertical opening into said safety glass frame, and said at least one projecting T-bar includes a leg and a cross piece connected with said leg, and said T-slot in said safety glass frame corresponds to dimensions of said at least one T-bar protruding from said eyeglass accessory.

4. Mounting means as set forth in claim 3, in which there are two spaced T-slots in said safety glass frame, and two spaced T-bars protruding from a frame portion of said eyeglass accessory.

5. Mounting means as set forth in claim 4 wherein:

said vertical opening of said at least one T-slot in said safety glass frame is disposed to one side of said safety glass frame.

6. Mounting means as set forth in claim 5 wherein:

said vertical opening in said T-slot in said safety glass frame extends within an inside surface of said safety glass frame and said eyeglass accessory is mounted on an inside of said safety glass frame.

7. Mounting means as set forth in claim 5 wherein:

said vertical opening of said T-slot in said safety glass frame extends within an outside surface of said safety glass frame and said eyeglass accessory is mounted on an outside surface of said safety glass frame.

8. Mounting means as set forth in claim 2 in which, said safety glasses include adjustable temples and said eyeglass accessory is without temples.

9. Mounting means as set forth in claim 2 in which:

said at least one T-slot has one portion which forms a vertical opening in the frame of said safety glasses frame, and one closed portion which extends transversely of said vertical opening into said safety glass frame, and said at least one projecting T-bar includes a leg that has a vertical extent which is greater than a thickness of said leg and a cross piece connected with said leg in which said cross piece has a vertical extent which is greater than a thickness of the cross piece, and said T-slot in said safety glass frame corresponds to dimensions of said at least one T-bar that protrudes from said eyeglass accessory.

10. Mounting means as set forth in claim 1 in which, said pair of glasses include adjustable temples and said eyeglass accessory is without temples.

* * * * *